(12) United States Patent
Gruzdev et al.

(10) Patent No.: US 7,524,317 B2
(45) Date of Patent: Apr. 28, 2009

(54) LASER SKIN PERFORATOR

(75) Inventors: Valentin A. Gruzdev, Moscow (RU); Pavel V. Efremkin, Ardsley, NY (US)

(73) Assignee: Innotech, USA, Inc., Tarrytown, NY (US)

( * ) Notice: Subject to any disclaimer, the term of this patent is extended or adjusted under 35 U.S.C. 154(b) by 779 days.

(21) Appl. No.: 10/842,597

(22) Filed: May 10, 2004

(65) Prior Publication Data

US 2004/0210279 A1 Oct. 21, 2004

Related U.S. Application Data

(63) Continuation of application No. 10/001,004, filed on Nov. 15, 2001, now Pat. No. 6,733,493.

(60) Provisional application No. 60/249,175, filed on Nov. 16, 2000.

(51) Int. Cl.
*A61B 18/20* (2006.01)

(52) U.S. Cl. .............................. 606/9; 606/13; 606/17; 600/573; 600/576; 600/578

(58) Field of Classification Search .............. 606/9–13, 606/16–19; 600/573, 575–578
See application file for complete search history.

(56) References Cited

U.S. PATENT DOCUMENTS

| 5,464,436 | A | * | 11/1995 | Smith | 607/89 |
| 5,908,416 | A | * | 6/1999 | Costello et al. | 606/9 |
| 5,947,957 | A | * | 9/1999 | Morris | 606/13 |
| 5,993,439 | A | * | 11/1999 | Costello et al. | 606/9 |
| 6,733,493 | B2 | * | 5/2004 | Gruzdev et al. | 606/9 |

* cited by examiner

*Primary Examiner*—Ahmed M Farah
(74) *Attorney, Agent, or Firm*—Lawrence G. Fridman

(57) ABSTRACT

A laser perforator for perforating skin of a patient and obtaining of blood samples consists of laser light source for producing an output laser beam, a focusing arrangement for focusing the output laser beam at a skin area selected for perforation, a guiding arrangement, a power supply unit and a retaining arrangement for retaining the skin area. The retaining arrangement is formed to intensify blood circulation in the skin area selected for perforation.

12 Claims, 14 Drawing Sheets

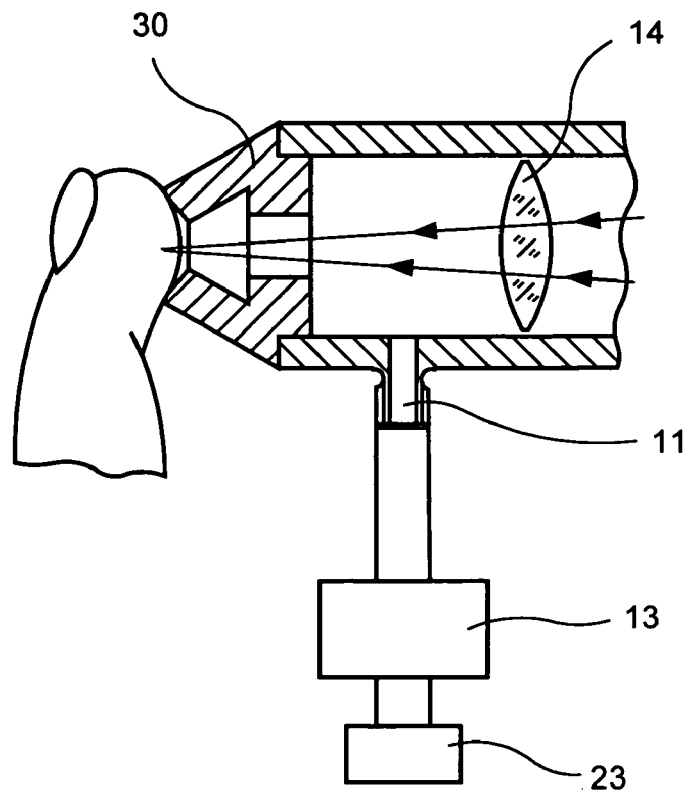
F I G. 1A
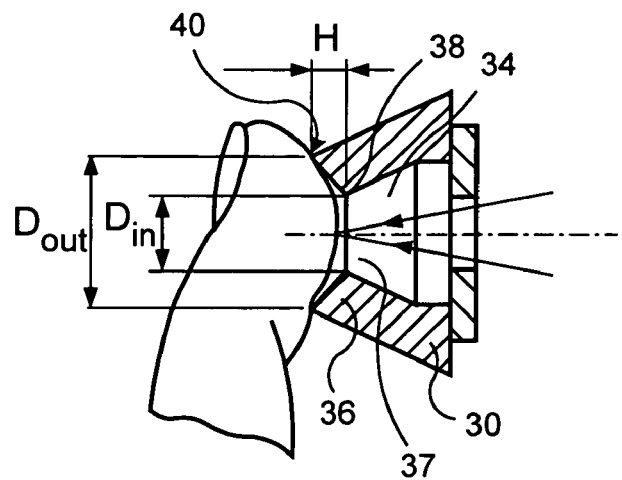
F I G. 2

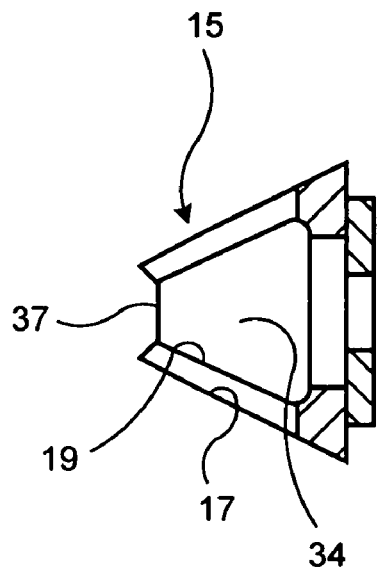
F I G. 2A
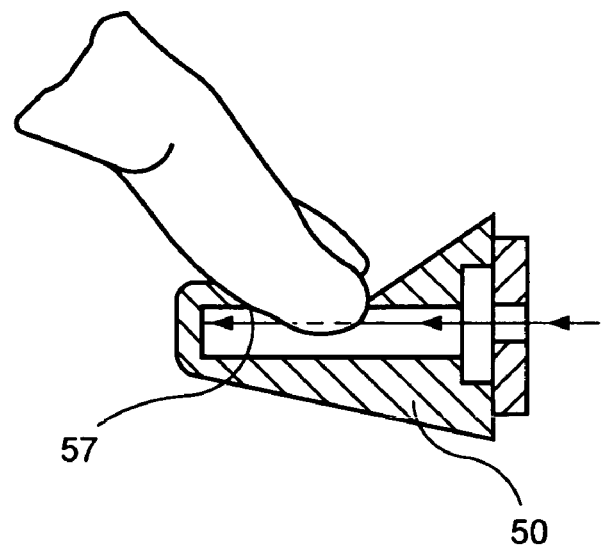
F I G. 3
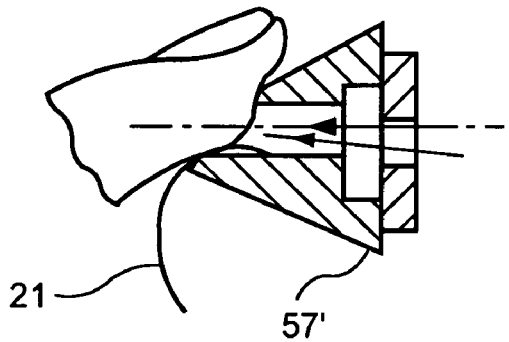
F I G. 4

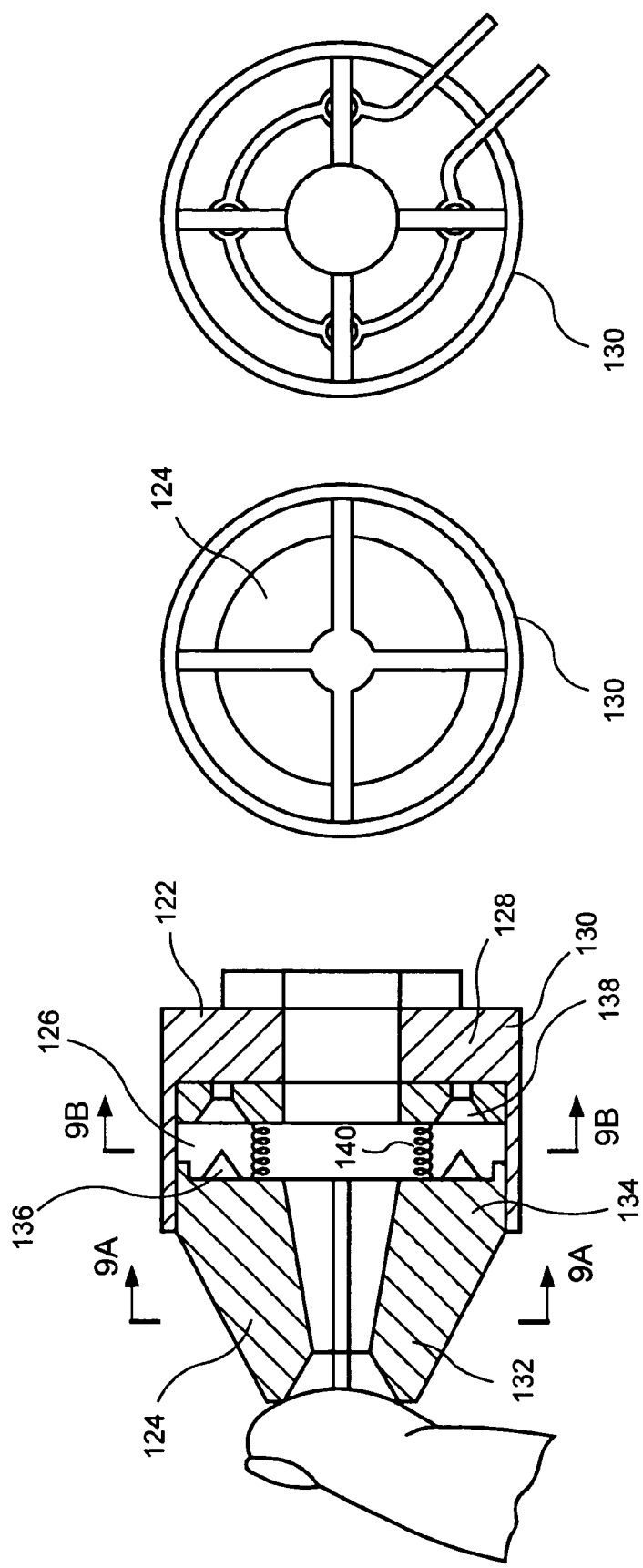

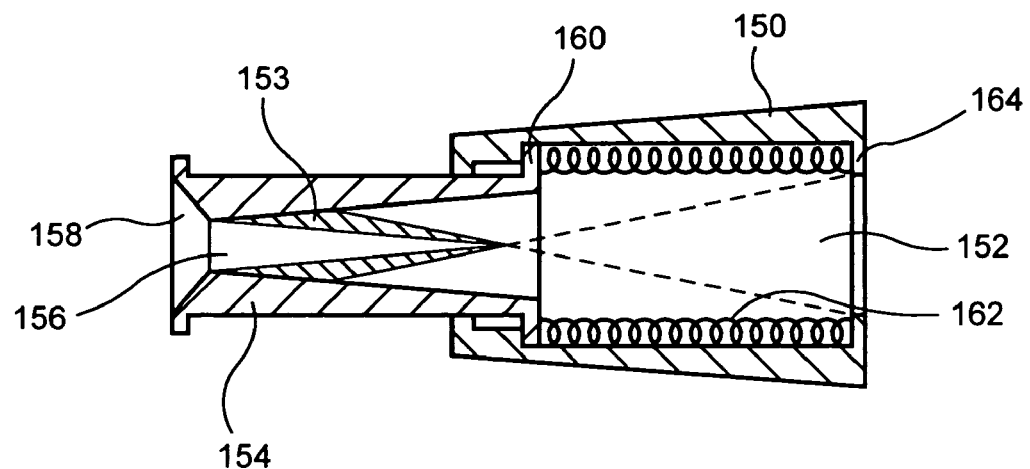
F I G. 10
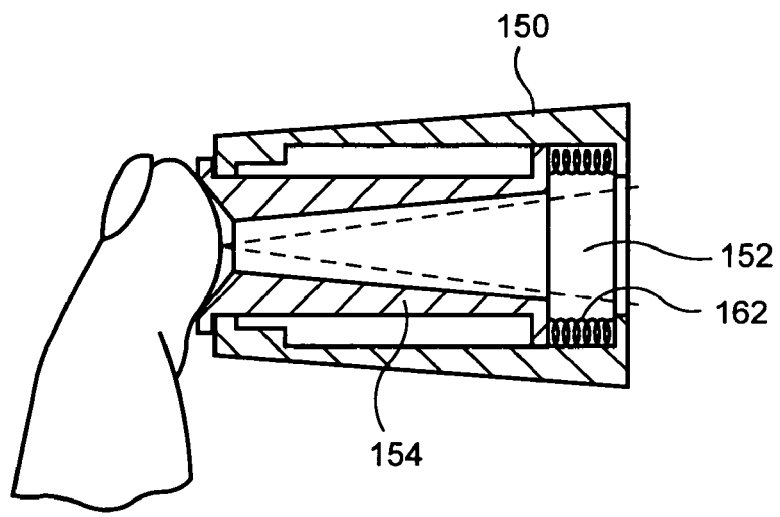
F I G. 11

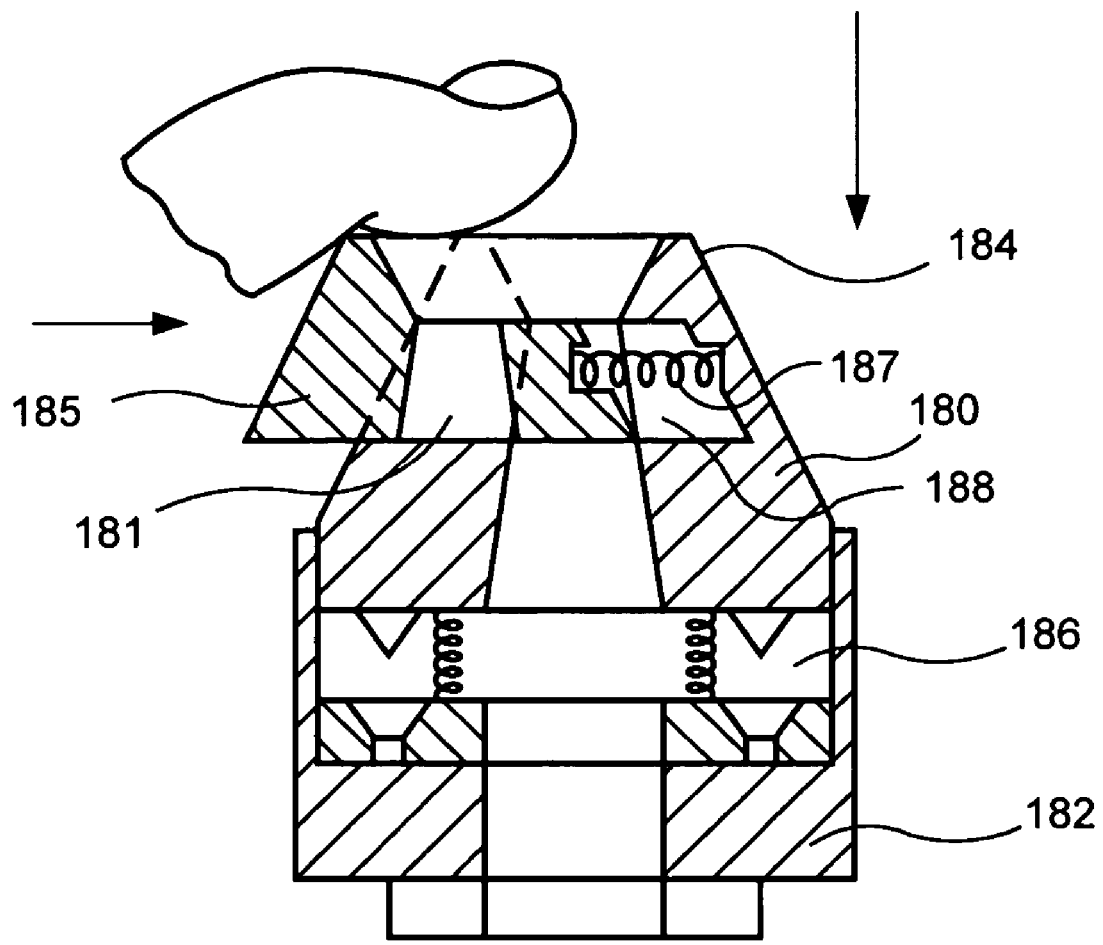
F I G. 12

LASER SKIN PERFORATOR

This application is a continuation of patent application Ser. No. 10/001,004 filed Nov. 15, 2001 now U.S. Pat. No. 6,733, 493 which currently is pending and which claims benefit under 35 USC 119(e) of the Provisional Patent Application 60/249,175 filed Nov. 16, 2000.

BACKGROUND OF THE INVENTION

1. Field of the Invention

This invention relates to laser medical device in general and in particular it relates to medical devices for no-contact perforation of a skin of a patient for obtaining blood samples.

2. Description of the Prior Art

Capillary blood sampling is a process for obtaining blood samples from the sub-dermal capillary beds of patients. The traditional methods for the collection of small quantities of blood from patients utilize mechanical perforation of the skin with sharp devices such as metal lancet or needle. This procedure has many drawbacks, two of which are the possible infection of health-care workers or the public at large with the device used to perforate the skin, and the costly handling and disposal of biologically hazardous waste.

Lasers have been used as an efficient precise tool in a variety of surgical procedures. Among sources of laser radiation, the rare-earth elements such as, for example, YAG (yttrium aluminum garnet) crystal doped with erbium (Er) ions are of interest for medicine.

As an active medium one can use various lasant materials to produce different wavelengths of laser light. These materials include, but are not limited to, rare-earth-doped oxide and fluoride laser crystals and glasses. Such crystals and glasses will be doped with impurities to fix the resultant wavelength of the laser.

In the case of lasers, the systems thereof generally include a light source for generating laser light, and optical components for directing the laser beam to a target. The laser source may produce continuous or pulsed laser energy output. The delivery of laser energy to a target specimen and subsequent vaporization of a portion of the specimen often produces byproducts, such as smoke, carbonized particles and/or splattered particles from the specimen. These byproducts pose a threat to the consistent operation of the laser system in that they may be deposited upon the objective optics of the system, thus damaging or altering the optical components, reducing output power, distorting the pattern of energy distribution within the light or laser beam, or otherwise contributing to the degradation of the system.

Methods and devices adapted for perforation of a skin tissue of a patient by means of a focused laser beam have been known in the prior art. The skin perforation is most effective when the wavelength of laser irradiation and the area of intensive absorption of optical emission by live tissue are matched. It is also important to prevent coagulation of a blood during treatment of live tissue by a laser beam. This can be achieved when yttrium-aluminum-erbium-garnet laser with laser emission wavelength of 2.94 microns and laser impulse duration between 50 and 500 microseconds is utilized by the perforation device. In the prior art perforation occurs when a laser beam is focused on the skin tissue, so that a small patch of skin at the area of focusing of the laser beam is evaporated.

Operation of certain medical devices for no-contact perforation of the skin of a patient while obtaining blood samples often produce significant pain and cause fear and apprehension in patients who anticipated a painful experience. Although modern designs of laser perforation devices attempted to eliminate such pain and apprehension, further reduction of patient discomfort would significantly increase the usefulness of new capillary sampling techniques. In the method and apparatus disclosed by U.S. Pat. No. 5,908,416, an attempt has been made to reduce pain in the course of perforation by providing a laser beam having a special shape. However, this approach increases the complexity of the optical system, leads to losses of the laser beam energy, makes the apparatus more expensive and difficult to manufacture. In this device, the increase in compensation of the laser energy should result in higher laser beam divergence ultimately causing skin burns at the area of perforation.

Thus, it has been a need for a laser perforation device capable of reducing pain and apprehension experienced by patients during the blood sampling procedures. It has been also a need for laser perforation devices which are protected from contamination by the products of skin tissue viporization.

SUMMARY OF THE INVENTION

One aspect of the invention provides a laser perforator for perforation of a skin of a patient and obtaining of blood samples. The perforator comprises a laser light source for producing an output laser beam, a focusing arrangement for focusing the output laser beam at the skin area selected for perforation, a guiding arrangement and a power supply unit. A retaining arrangement is provided for intensifying blood circulation in the skin area selected for perforation. The skin retaining arrangement consists of a substantially hollow intermediate region formed with a flexible peripheral wall. The intermediate region is interposed between a forwardly positioned engaging cup and rearwardly located base wall. A base member is positioned within the substantially hollow intermediate region between the engaging cup and the base wall. The flexible peripheral wall is deformable to substantially reduce a volume of the intermediate region causing pressure increase thereinside. The skin retaining arrangement also includes a pressure adjustment device for pressure adjustment within the intermediate region. After the pressure adjustment has taken place, a low pressure zone is formed within the intermediate region, so as to create suction for bringing at least a portion of the skin area deeper into the engaging cup. The pressure adjusting arrangement can be in the form of a valve and the biasing member is provided to facilitate a return of the deformed intermediate region to its initial undeformed position.

As to another aspect of the invention, the rear wall of the engaging cup is formed with an opening provided for passage of the laser beam. An optical membrane preventing fluidal communication between the engaging cup and an inner area of the perforator containing the laser source and the focusing arrangement can be provided with the opening. The shield is made of a material translucent to the laser irradiation.

As to a further aspect of the invention, a laser energy delivered to the skin of a patient can be adjusted by means of an optical member having the variable thickness along its length. The optical member is made of a material having predetermined laser irradiation transmission characteristics. The optical member is positioned between the skin area to be perforated and the laser source. The optical member can have a wedge-shaped configuration with a substantially cylindrical outer wall and can be rotationally positioned between the laser source and the focusing arrangement. In another embodiment of the invention, the optical member is moved transversely to the direction of the laser beam.

A still another aspect of the invention provides a device which prevents unintended activation of the perforator. This device comprises a plurality of independent engaging segments slidably arranged along the longitudinal axis of the cup. The distal portion of the segment forms a part of a switch operable between open and closed positions. In the open position, the distal portions of the engaging segments are spaced from a conductive plate position at a rear wall of the engaging cup, so as to disconnect an electrical supply line of the laser source. In the closed position, the distal portions of the engaging segments engage the conductive plate, so as to activate the electrical supply line of the laser source. The device can include a sliding member movable within a plane transverse to the direction of the laser beam, so that in a standard position of the device the sliding member blocks a central passage of the perforator preventing an accidental discharge of the laser beam.

The engaging cup can be formed with a substantially hollow interior cavity and is defined by at least a side wall thereof. An engaging aperture can be formed within the side wall, so that the laser beam entering the substantially hollow interior area is directed tangentially to the skin area protruding through the engaging aperture, so as to generate an elongated slit within the perforated area of the skin. Alternatively, the engaging aperture adapted for receiving the skin area can be formed at the front portion of the engaging cup, so as to be positioned at an angle to the direction of the laser beam entering the interior area.

BRIEF DESCRIPTION OF THE DRAWINGS

FIG. 1A shows a front area of the perforator having a suction arrangement;

FIG. 2 shows an engaging cup of the perforation device;

FIG. 2A shows another embodiment of the engaging cup;

FIG. 3 shows a further embodiment of the engaging cup;

FIG. 4 shows still another embodiment of the engaging cup;

FIG. 9 is a sectional view of the front portion of the perforation device showing a safety feature of the invention;

FIG. 9A is a sectional view according to section line 9A-9A of FIG. 9;

FIG. 9B is a sectional view according to section line 9B-9B of FIG. 9;

FIG. 10 is a sectional view showing another safety feature of the invention in an expanded position;

FIG. 11 shows the safety feature of FIG. 10 in an operational position;

FIG. 12 shows another safety feature of the invention;

DESCRIPTION OF THE PREFERRED EMBODIMENT

Reducing pain experienced by a patient during the skin perforation procedure is a complex undertaking which requires consideration of the following factors: safe and easy-to-use design of the apparatus, selection of the area of perforation, pre-treatment of the skin site prior to the perforation procedure and adjustment of the laser beam intensity. It is also necessary to define an optimal level of energy for each individual patient and provide proper focusing of the laser beam within the zone of perforation.

In minimizing of pain during the skin perforation, it is essential to reduce the density of the laser energy at a point of perforation and to minimize the size of a wound in a skin tissue of the patient, while keeping the amount of blood excretion at a constant level. In one embodiment of the invention this task is accomplished by stimulation of a blood flow within the skin site selected for perforation, so that even a small perforation may yield the required amount of blood. The blood flow stimulation in the area of perforation can be achieved by bringing this area of the skin within the engaging opening of the skin retention device.

Figure 1:
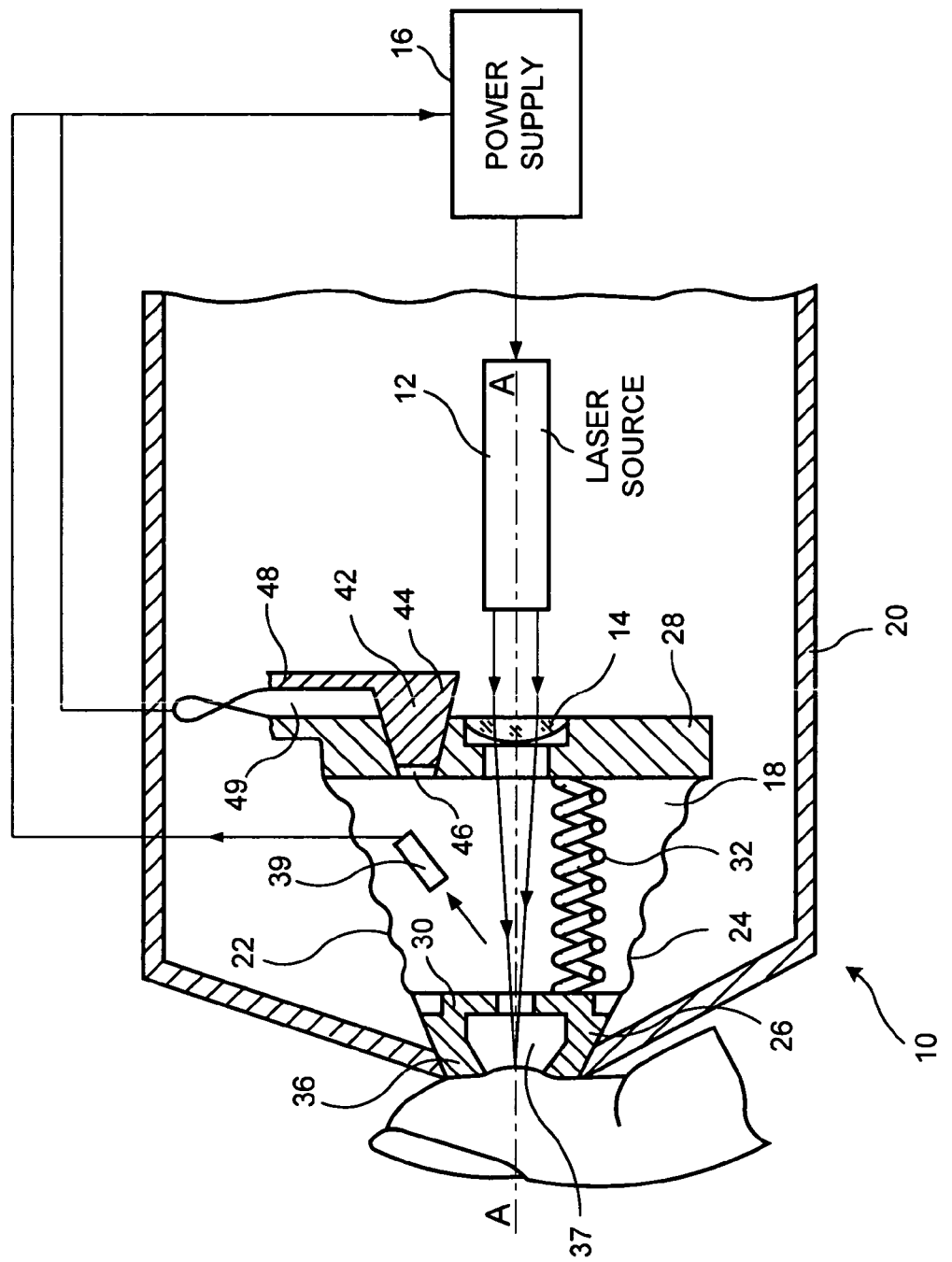
FIG. 1 is a schematic diagram of a laser perforator of the invention including a skin retention device.

Turning now to FIG. 1 showing a laser skin perforation device or laser skin perforator 10 formed with a skin retention device adapted to stimulate a blood flow in the area of perforation. Among major elements of the laser skin perforator illustrated in FIG. 1 are: an impulse-type laser source 12 producing in an output of a laser beam; a focusing arrangement 14 for focusing the laser beam to produce high energy fluence on a particular section of skin surface; a power supply block 16 and a device 18 to retain the selected perforation site within a focusing zone of the laser beam.

The impulse-type laser source 12 and the skin retention device 18 are typically situated within the housing 20 of the perforator. The skin retaining device 18 is positioned at a front portion of the housing with the impulse-type laser source 12 situated rearwardly therefrom. The skin retention device 18 consists of a substantially hollow intermediate region 22 having a flexible exterior wall 24 which is situated between proximal 26 and distal 28 portions thereof. At least one spring or biasing member 32 extends within the intermediate region between the proximal and distal portions. In the embodiment of FIG. 2 the proximal portion 26 of the retaining device is in the form of an engaging cup adapted to engage a skin site to be perforated during the blood collection procedure.

As best illustrated in FIGS. 2 and 2A, a typical engaging cup 30 has a frustoconical configuration and is formed with a substantially hollow interior space 34. For better engagement with the skin site to be perforated, such as for example, a finger of a patient, the front tip 36 of the engaging cup is provided with an engaging aperture 37 having substantially circular inner 38 and outer 40 areas positioned within the planes spaced from each other and substantially normal to the longitudinal axis of the engaging cup. The ratio between a diameter of the outer area 40—($D_{out}$) and a diameter of the inner area 38—($D_{in}$) has been chosen to be greater than 7:3 ($D_{out}$:$D_{in}$>7:3). The distance between the inner and outer areas varies between 1.0 and 5.0 millimeters.

A pressure relief valve 42 is provided within the distal portion 28 of the skin retention device. As best illustrated in FIG. 2, the pressure relief valve 42 consists of a semi-conical adjusting member 44 adapted for slidable engagement with a receiving opening 46 provided within a wall of the distal portion 28. A handle 48 extends outwardly from the adjusting member 44. A switch 49 is interposed between the handle 48 and an exterior wall of the distal portion. Although a specific design of the relief valve 42 has been discussed hereinabove, it should be understood that utilization of other conventional valve arrangements in the apparatus of the invention is also contemplated.

In operation, the initial pressure is applied when the operator presses the front tip 36 of the engaging cup 30 against an area of the skin tissue adapted for perforation. This causes the initial blood inflow to the perforation area. In view of the flexibility of the exterior wall 24 of the intermediate region, when greater forces are being applied by the operator further pressing of the engaging cup 30 against the skin, the proximal portion 26 is brought closer to the distal portion 28 causing substantial reduction of the hollow intermediate region 22 and the respective pressure increase thereinside. This results in the opening of the relief valve 42, so that the pressurized gas from the interior of the skin retention device is released into the atmosphere. When the application of force against the skin of the patient is being discontinued, the flexible wall 24 of the intermediate region driven by the biasing member or spring 32 returns to its original expanded position (see FIG. 1). During this motion, a low-pressure zone is developed within the hollow, intermediate region 22, causing closing of the valve 42. This in turn develops suction, which brings the perforated skin area deeper into the engaging aperture 37 of the proximal portion. This results in further deformation of the skin and the additional inflow of blood to the perforated area. Upon closing of the valve 22, the handle 48 is brought into the vicinity of the distal portion 28 activating the switch 49. This activates the power supply block 16 and energizes the laser source 12 to generate the laser beam causing the skin perforation.

Turning now to FIG. 1A showing another embodiment of the invention, in which an inner space area between the engaging cup 30 and the focusing arrangement 14 is connected by means of a pipe outlet 11 with a suction arrangement 13. To avoid contamination of the inner area of the apparatus, skin evaporation and other unwanted products developed during a blood sampling procedure are removed and accumulated at a filter 23.

In the embodiment of FIG. 1, to prevent accidental activation of the laser source 12, a photo-sensor or electrical capacity sensor 39 can be provided within the hollow intermediate region 22 of the skin retention device. Activation of the power supply block 16 does not occur for as long as the light penetrates through the engaging aperture 37 into the hollow intermediate region 22 and register at the sensor 39. Thus, activation of the device is prevented for as long as the engaging aperture 37 is spaced from the skin of a patient. The sensor 39 allows the power supply block to send a high voltage impulse to the laser source 12 only when the engaging aperture is blocked by the skin site and ambient light can not penetrate into the hollow intermediate region.

The sensor 39 can also be in the form of a photo-resistor or photo-diode that is activated when a predetermine level of illumination intensity is reached within the interior of the intermediate region. In the alternative embodiment, the function of the sensor may be performed by a device that registers electrical capacity disturbances caused by positioning of the selected skin area at the engaging aperture 37. In the embodiment of FIG. 1, the light sensor 39 forms a part of the inner area of the intermediate region of the skin retaining device. However, it should be clear that positioning of the sensor in other parts of the laser perforation device is within the scope of the invention.

Turning now to FIGS. 3 and 4, which illustrate alternative, embodiments of the engaging cups providing further possibilities of reducing pain experienced by patients during the skin perforation. The size of the skin perforation may be adjusted by changing an angle at which a laser beam is directed to the skin surface. Longitudinal perforations or slits often generate the required amount of blood at a smaller depth of penetration into the skin tissue. Since concentration of nerves decreases near the surface of the skin, this technique often causes less pain during the blood sampling.

In the embodiment of FIG. 3, the engaging cup 50 is in the form of an elongated cone-shaped member with a closed front end and a substantially hollow interior. An elongated engaging aperture 57 extends within a sidewall of the engaging cup 50 and is spaced from its longitudinal axis. Upon positioning of a finger, or other skin surface adapted for perforation, within the elongated engaging aperture 57, only a limited area of the skin extends through the aperture into the hollow interior. Thus, an elongated engagement area is formed between the skin and the aperture. As illustrated in FIG. 3, the laser beam is directed tangentially to the skin area penetrating into the hollow interior of the cup. Thus, a longitudinally extending slit having a limited depth of penetration into the skin tissue is produced.

In the embodiment illustrated in FIG. 4 the inner and outer areas of the engaging aperture 57 are transverse to the direction of the laser beam and positioned at an angle other than normal to the longitudinal axis of the engaging cup. More specifically, the planes of the inner and outer areas are positioned at an angle to the direction of the laser beam. This arrangement typically provides an oval-shaped engagement area between the skin and the engaging aperture 57. Thus, in the embodiment of FIG. 4, the laser beam is exposed to perforated skin area at an angle; so as to form an elongated slit, which extends near the surface of the skin.

As best illustrated in FIG. 4, a disposable test strip 21 can be provided at the outer area of the engaging aperture 57 of the engaging cup for visual and/or quantitative express blood analysis.

In the invention the engaging cup can be an integral part of the laser skin perforator in general and/or the skin retaining device in particular. Alternatively, the engaging cup can be formed as a disposable unit removable from the perforation device. In this instance, the engaging cup can be utilized as a disposable container adapted for collection of the produced blood samples. An example of such disposable engaging cup 15 is illustrated in FIG. 2A. A blood sample is actually collected within an inner hollow area 34 of the engaging cup which is located rearwardly of the front engaging aperture 37. To facilitate a visual evaluation of the collected blood, a side wall 17 of the engaging cup can be made from a transparent material. The interior surface 19 of the side wall of the container can be at least partially covered by a coating which is adapted to indicate the presence of sugar, the level of cholesterol, etc. during the express blood analysis. In order to facilitate handling of the device by an operator, an exterior of the side wall can be at least partially covered by a non-slippery material.

To neutralize unpleasant odor and to further protect the components of the perforation device from contamination by the products of skin evaporation, the interior surface 19 of the engaging cup can be covered by a layer of an absorption material. One example of such material is activated carbon.

It is known that the skin thickness and the ability to yield blood may vary substantially from one patient to another. It is also known that greater laser energy is required for perforation of a hard skin compared to a soft, gentle skin of a patient. When during the blood sampling a laser energy of equal density is applied indiscriminately to all patients, individuals with soft gentle skin typically suffer unnecessarily greater pain. Adjusting the density of the laser energy to the levels minimally required for perforation, constitutes an important prerequisite for minimizing the pain experienced by a patient. The prior art laser skin perforators provide various electronic devices capable of adjusting the supply of energy for energizing laser sources and to regulate the level of energy delivered by a laser beam to the skin of a patient. Such electronic devices are often complicated and not totally reliable.

Figure 5:
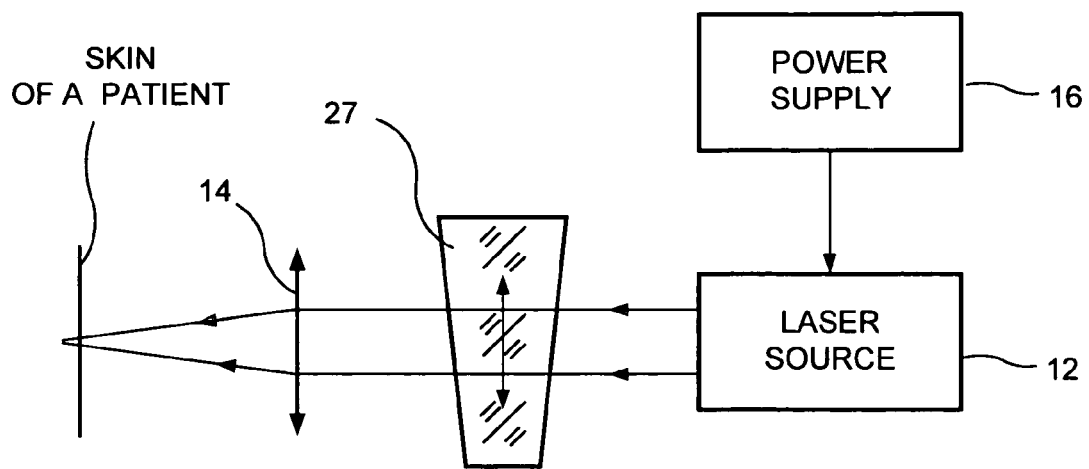
FIG. 5 is a schematic diagram showing application of an optical member used in the perforation device.
Figure 6:
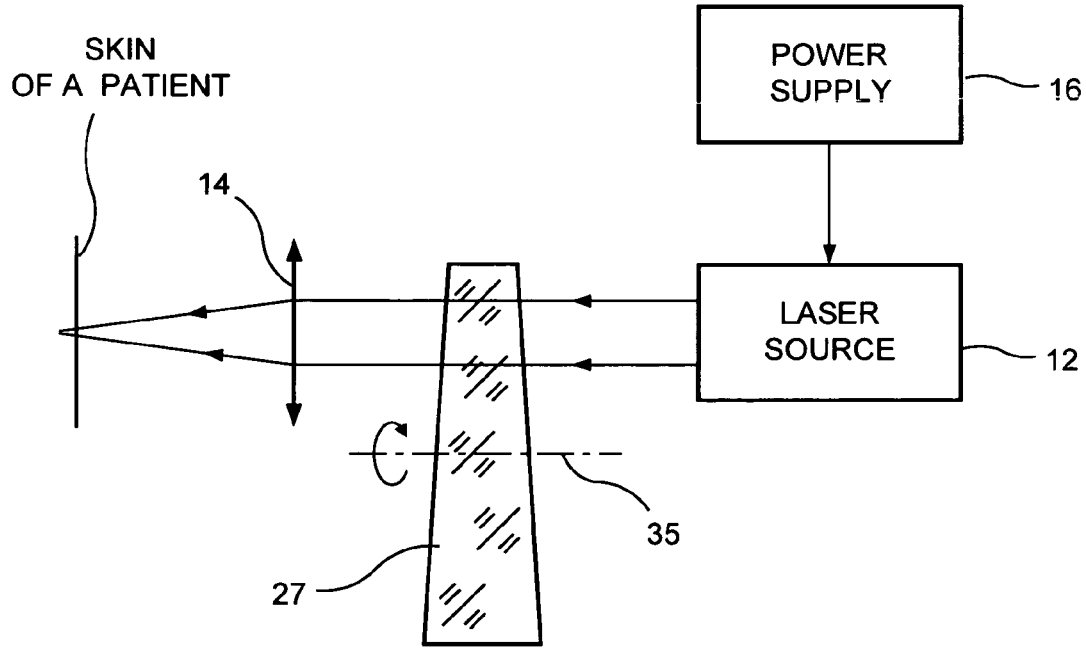
FIG. 6 is a schematic diagram illustrating another application of the optical member.
Figure 6A:
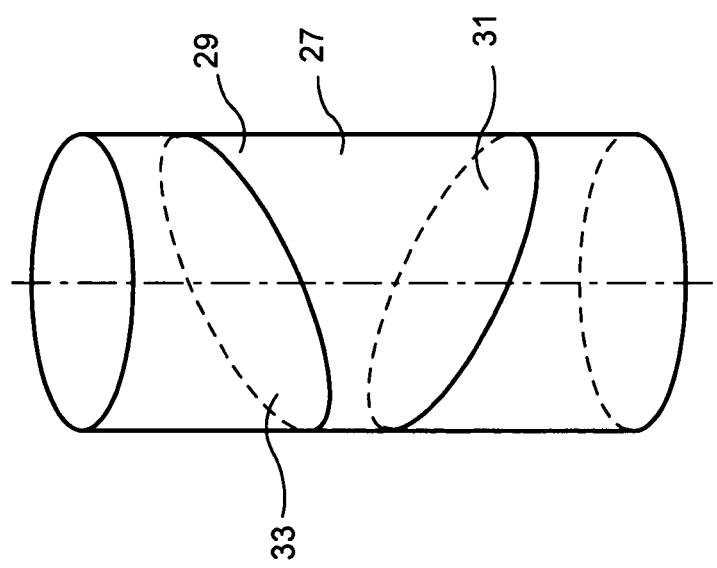
FIG. 6A illustrates formation of the optical member.

Turning now to FIGS. 5, 6 and 6A, which illustrate a further embodiment of the invention including an optical member 27 of variable thickness. The optical member is typically positioned between the skin and the laser source 12. The optical member 27 can also be positioned between the skin and the focusing arrangement 14, or between the focusing arrangement 14 and the laser source 12. The optical member 27 is formed having a wedge-shaped configuration and is made of a material having predetermined transmission characteristics at the required laser irradiation wavelength. As illustrated in FIG. 6A the optical member can be formed when a cylindrical body is cut by a plane or planes which are disposed at an angle to a longitudinal axis thereof. The typical body of the optical member consists of a substantially cylindrical outer surface 29 and first 31 and second 33 bases interposed to each other at an angle. Alternatively, one of the bases can be substantially perpendicular to the longitudinal axis of the optical member. Other alternative designs of the optical member are within the scope of the invention. As illustrated in FIG. 5, the laser energy delivered to the skin can be adjusted when the optical member 27 is moved transversely to the direction of the laser beam. In another embodiment (see FIG. 6) the adjustment of the laser energy is achieved when the longitudinal axis 35 of the optical member is spaced from and parallel to the direction of the laser beam and the optical member 27 is rotated about the longitudinal axis.

Figure 7:
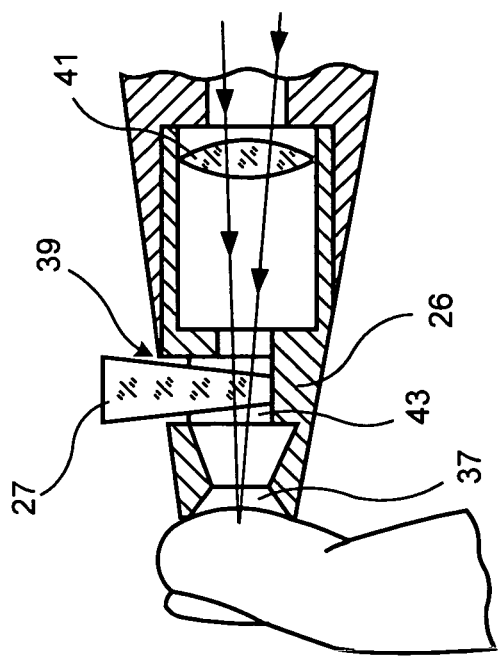
FIG. 7 shows a front portion of the perforation device with the optical member.

Turning now to FIG. 7 showing a portion of the laser skin perforator with the engaging cup 26 forming an integral part of the housing 20. In this arrangement the location of the focal point of the laser beam is fixed at the area of engagement between the engaging opening 37 of the cup and the skin area adapted for perforation. The engaging cup is formed with an adjustment assembly 39 situated forwardly of the focusing arrangement 41. The adjustment assembly consists of a receiving recess 43 and an optical member 27. As discussed hereinabove the optical member 27 can have a wedge-shaped configuration with a substantially cylindrical outer surface. The optical member is rotatable about its longitudinal axis and extends into the inner cavity of the engaging cup through the receiving recess 43 formed within a side wall thereof. In the embodiment of FIG. 7 the rotational axis of the optical member 27 is substantially parallel to the longitudinal axis of the housing 20. To adjust the level of the laser beam energy, the optical member 27 is rotated, so as to expose portions of the optical member having various thickness to the laser beam. In this respect, when a greater level of energy is required for perforation of a thick skin, a portion of the optical member 27 having the reduced thickness is exposed to laser beam and vice-versa. The optical member 27 also prevents contamination of the interior of the of the perforation arrangement including the focusing arrangement by the skin evaporation products.

Figure 8:
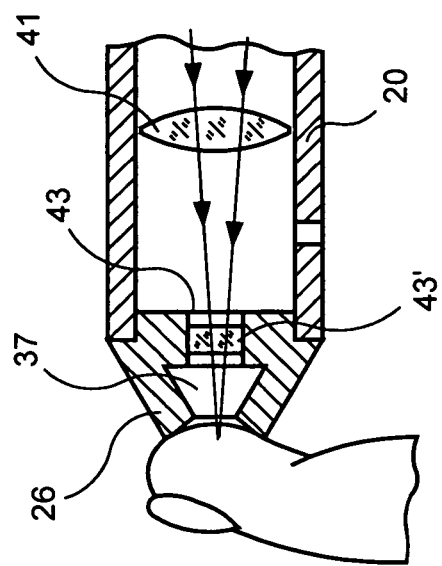
FIG. 8 shows a modified front portion of the perforation device.

As best illustrated in FIG. 8, the engaging cup includes an optical membrane 43' which is made of a material having predetermined transmission characteristics at the required level of irradiation. This membrane 43' has a prefixed thickness and is capable of reducing the laser energy passing therethrough to a predetermined level. Such arrangement allows to choose an optimal level of laser energy delivered to the skin area by selecting a replaceable engaging cup having an optimal thickness of the membrane 43'.

The rear opening of the engaging cup can formed having a variable inner diameter which typically do not exceed the size of the outer periphery of a laser beam. By choosing the size of such inner opening 43 to meet the needs of a specific patient, the density of the laser energy at the point of perforation may be adjusted.

Although the above-discussed embodiments have been described with a finger used in the perforation procedure, it should be understood that skin sites of the body other than the fingers can be utilized in the skin perforation procedure.

Turning now to FIGS. 9, 9A and 9B showing a device of the invention adapted to prevent an accidental activation of the laser perforation device. In this embodiment the engaging cup 130 operates as a switch capable of connecting and disconnecting a power supply to the laser source. The cup 130 consists of a base 122 and a plurality of engaging segments 124. The base is formed with an inner cavity 126 extending forwardly from a rear wall 128 and is adapted to slidably receive the plurality of the engaging segments. Although any reasonable number of the segments is contemplated, in the embodiment of FIG. 9, the engaging cup 130 is formed with four segments symmetrically positioned along its longitudinal axis. Each engaging segment consists of at least a front part 132 adapted for engagement with a skin of a patient and a rear part 134 adapted for slidable movement within the inner cavity 126. The rear part 134 of each segment has an engaging element or contact 136 extending outwardly therefrom and adapted for engagement with the respective openings 138 in the conducting plate associated with the rear wall 128 of the base. When pressed, each segment 124 slides within the inner cavity 126 along the longitudinal axis of the cup and independently from other segments. A biasing member or a spring 140 is positioned between the rear end of each segment and the rear wall of the cup. As illustrated in FIG. 9, when a skin initially engages the front parts 132 and no substantial inwardly directed forces are exerted on the engaging segments, the resistance of the biasing members or springs 140 is sufficient to keep the rear parts 134 of the segments including the contacts or engaging elements 136 separated from the openings 138 in the conducting plate. In this condition the electric line supplying energy from the power unit to the laser source is disconnected. The laser source is activated only when each of the engaging segments is firmly pressed by the skin, so that the rear part 134 including the contact 136 of each segment is moved within the inner cavity and each projection or contact 136 engages the respective openings 138. As an alternative, the engaging cup can be formed as a solid unitary member without being separated on individual engaging segments.

Turning now to FIGS. 10 and 11, illustrating another embodiment of the engaging cup of the invention, which consists of a base member 150 formed with a hollow inner space 152 and an elongated outer member 154 telescopically positioned within a hollow inner space of the base member. A central elongated opening 156 extends through the entire length of the outer member 154 from an engaging recess 158 and a flange 160 provided at a distal portion thereof. The engaging recess 158 is shaped to engage a skin area, such as a finger of a patient, adapted for perforation. A spring or biasing member 162 is interposed within the inner hollow space between the flange 160 and a rear wall 164 of the base member. The focal point of the laser beam is fixedly located within at the front part of the base member. In the expanded position (see FIG. 10), the outer member 154 including the engaging recess 158 extends outwardly from the inner hollow space 152 of the base member. To initiate the perforation process the skin area adapted for perforation is initially placed within the engaging recess 158. Then, the inwardly directed force is exerted on the outer member 154, so as to suppress the resistance of the biasing member 162 causing movement of the outer member 154 onto the hollow space 152. When the outer member 154 reaches its submerged position within the base member (illustrated in FIG. 11), the selected skin area is exposed to the focal point of the laser beam causing its instantaneous perforation. For the additional safety the inner surface of the central opening 156 of the outer member may be coated by a material 153 having high absorption at the wavelength of a laser irradiation. In the embodiment of FIGS. 10 and 11, the perforation does not occur until the outer member is firmly pressed and moved to the submerged position, so that the skin area adapted for perforation is situated at the fixedly positioned focal point of the laser beam.

Another device adapted to prevent accidental activation of the laser skin perforator is illustrated in FIG. 12. The construction of this device is similar to the device discussed hereinabove with reference to FIG. 9. However, in the embodiment of FIG. 12 the engaging cup 180 is provided with a slot 188 extending within a plane substantially parallel to the rear wall 182 of the base portion. A slidable member 185 having an opening 181 is provided for engagement with a slot. A biasing member 187 is interposed between the interior of the slot 188 and the slidable member 185. In a standard extended position (illustrated by solid lines in FIG. 12) the sliding member protrudes outwardly from the slot. In this condition the opening 185 is shifted sidewardly, so that the main passage of the engaging cup is blocked by a solid portion of the slidable member 185. In this condition the downward motion of the engaging cup 180 is prevented by the extending portion of the slidable member 185. Therefore, the accidental discharge of the laser beam irradiation is prevented. In order to perform the skin perforation, the operator presses the extending portion of the sliding member inwardly, such that the opening 185 coincides with the main passage and the entire engaging cup can be moved downwardly to activate the contact in the manner described with reference to the embodiment of FIG. 9.

In order to facilitate this operation, the member 57, as well as other members of the cup 26, may be coated by non-slipping material. For additional safety, a part of the internal surface of cup 26 may be coated by a material having a high level of absorption of a laser irradiation (see element 153 of FIG. 10). Such arrangement does not allow activation of the laser when the cup is not actually pressed against the skin site to be perforated, but accidentally pressed, for example, by a child.

Another embodiment of the invention provides a skin perforation device having a focusing system enabling a user to focus a laser beam at a predetermined depth in the skin tissue to be perforated. As discussed in more detail hereinbelow, such targeted focusing of the laser beam within the skin tissue is an important condition for reducing pain during the perforation process.

Figure 13:
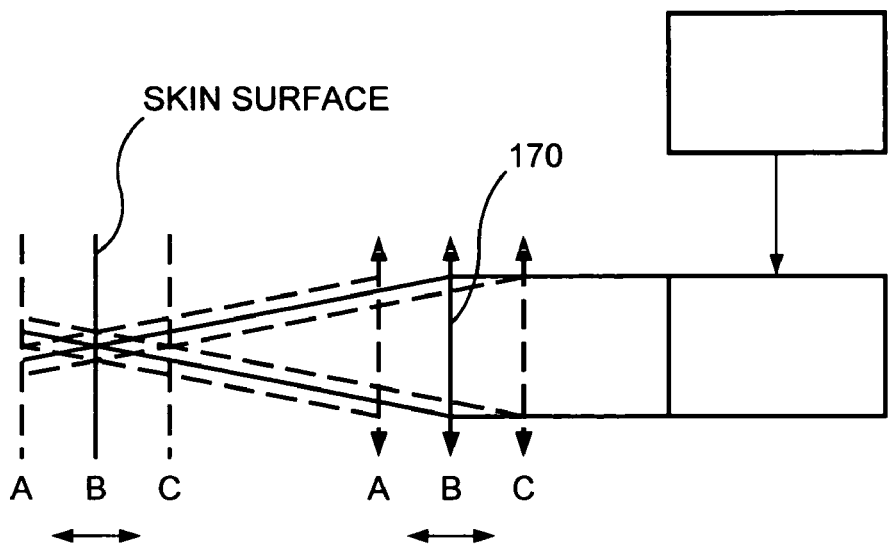
FIG. 13 is a schematic diagram showing various positions of a focusing arrangement.

In the arrangement illustrated in FIG. 13 a skin area adapted for perforation is fixedly positioned at a predetermined distance from the laser source and the focusing system which includes a focusing lens 170 movable along an axis of the laser beam. FIG. 13, in this respect, is a schematic diagram showing three positions A, B and C of the focusing arrangement or the lens 170 and in its motion along the longitudinal axis of the laser beam and three respective locations of the focal point of the laser beam a, b and c. These illustrated positions correspond to the wound formations discussed hereinbelow with reference to FIGS. 13A, 13B and 13C. In the position A,a (see FIG. 13), the focal point of the laser beam is situated at a predetermined depth within the skin tissue. In the position B,b the laser beam is focused at the surface of the skin, whereas in the position C,c the focal point is spaced from and separated by a gap from the skin surface.

Figure 13A:
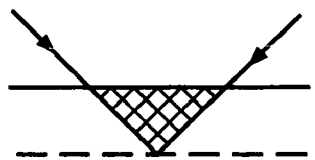
FIG. 13A is a diagram illustrating a wound developed in a skin of a patient when the lens is in the position A shown in FIG. 13.
Figure 13B:
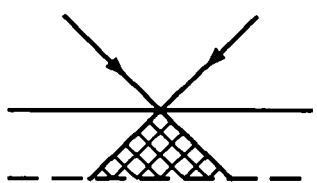
FIG. 13B is a diagram illustrating a wound developed when the lens is in the position B shown in FIG. 13.
Figure 13C:
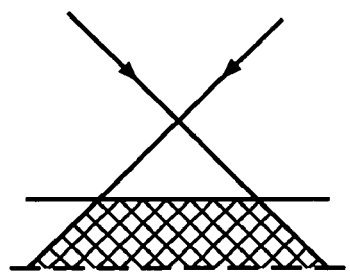
FIG. 13C is a diagram illustrating a wound developed when the lens is in the position C shown in FIG. 13.

As indicated hereinabove, FIGS. 13A, 13B and 13C are the schematic representation of wounds in the skin of a patient produced at the respective positions of the focusing lens. FIG. 13A illustrates the wound when the focus of the laser beam is positioned within the tissue and spaced from the skin surface; FIG. 13B shows the wound when the laser beam is focused at the skin surface; whereas the wound of FIG. 13C is developed when the focus of the laser beam is positioned outside of the skin surface.

In order to minimize pain experienced by a patient during the perforation procedure, it is desirable to focus the laser beam at a predetermined depth within the tissue (see FIG. 13A), and not at the surface or spaced from the surface (as illustrated in FIGS. 13B and 13C). This is because, during the perforation the laser beam evaporates live tissue and forms a stream of high speed, pressurized gases which are trying to escape the perforation site. Upon positioning of the focal point of a laser beam at a predetermined depth within the skin tissue (see FIG. 13A), the resulting wound is formed having a cone-shaped configuration with its tip situated within the skin tissue and wide opening positioned at the skin surface. Such shape of the wound facilitates escape of the gases and skin tissue evaporation products without causing unnecessary pressure and irritation to the surrounding nerve formations. The optimal depth of the focusing point depends on the skin condition of a patient and the amount of the required blood. In the pediatric applications or when tests require a small amount of blood, for example in glucose testing for diabetic patients, the depth of the focal point between 0.12 millimeters (end of epidermis) and 1.5 millimeters is recommended. When a greater amount of blood is required for testing, the focal point should be spaced between 1.5 and 4.0 millimeters from the skin surface. To evaporate a double hatched area shown in FIG. 13A while the focal point of the laser beam is situated at the depth between 0.12 and 4.0 millimeters within the skin tissue, the diameter of the laser beam should be between 1.0 and 3.0 millimeters.

In the embodiment of FIG. 13B, during the perforation procedure the laser beam is focused at the surface of the skin. In this condition the laser beam burns out a small opening at the surface of the skin. The resulted wound is formed having a conicaly-shaped configuration with a broad base positioned deeply inside the skin tissue and a small opening on the skin surface. The gases and products of inner tissue evaporation are allowed a very limited time to escape through this small opening. This results in a high pressure products build up within the wound causing substantial pain and a hemorrhage (bruise) to the surrounding tissue.

In the condition illustrated in FIG. 13C, the focal point of the laser beam is spaced from and positioned beyond the skin surface. This condition results in the wound having a broad base situated within the skin tissue with a substantially narrower opening at the skin surface. The gases and products resulted from evaporation of the double hatched skin area cannot efficiently escape through the relatively small opening at the skin surface. This inevitably resulted in a considerable pressure being exerted on the inner skin tissues causing considerable pain. As illustrated in FIG. 13C, the beam reaches the skin surface unfocused and then broadens substantially. Since the skin area to be evaporated is increased in size, the level of the laser beam energy should be increased accordingly causing greater pain. If more blood needs to be collected, the pain increases proportionately to the increase in the level of applied laser energy.

The optimal focusing of the laser beam can also be achieved through utilization of the replaceable engaging cups which were discussed with reference to FIGS. 1, 2, 3 and 4. In a laser perforation device having a preset location of the focal point of the laser beam, a proper positioning of the perforated skin site can be achieved by means of selection of an appropriate engaging member having the required length. Thus, through the selection of shorter or longer engaging cups it is possible to place the engaging area of the engaging cup and the skin site associated therewith in such a manner that the focal plane is located at the predetermined depth within the skin tissue (see FIG. 15). Therefore, the required focusing can be achieved for each individual patient with the skin sites to be selected at practically any part of the human body.

Figure 15:
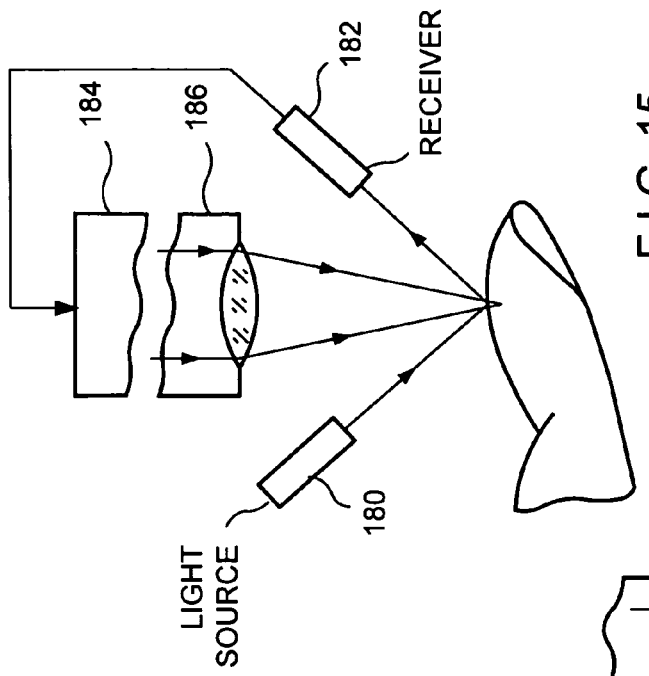
FIG. 15 illustrates another focusing arrangement of the invention.
Figure 14:
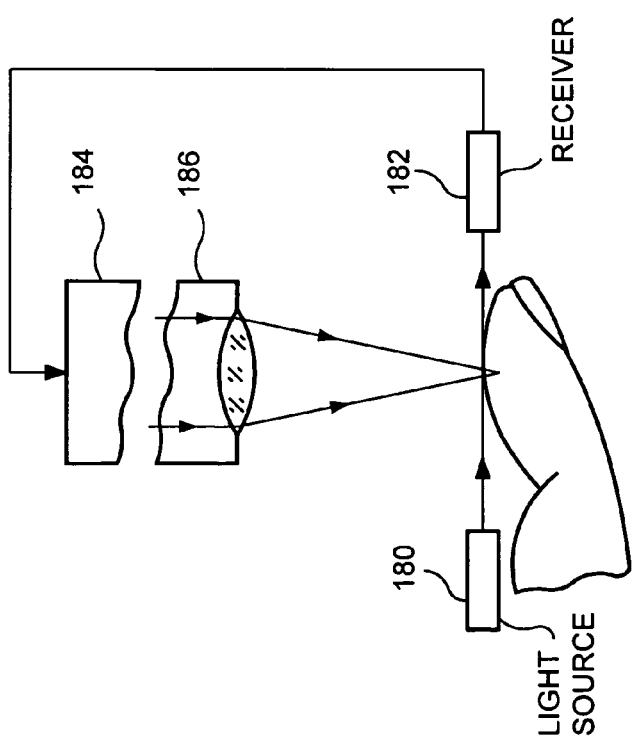
FIG. 14 illustrates a focusing arrangement of the invention.
Figure 17:
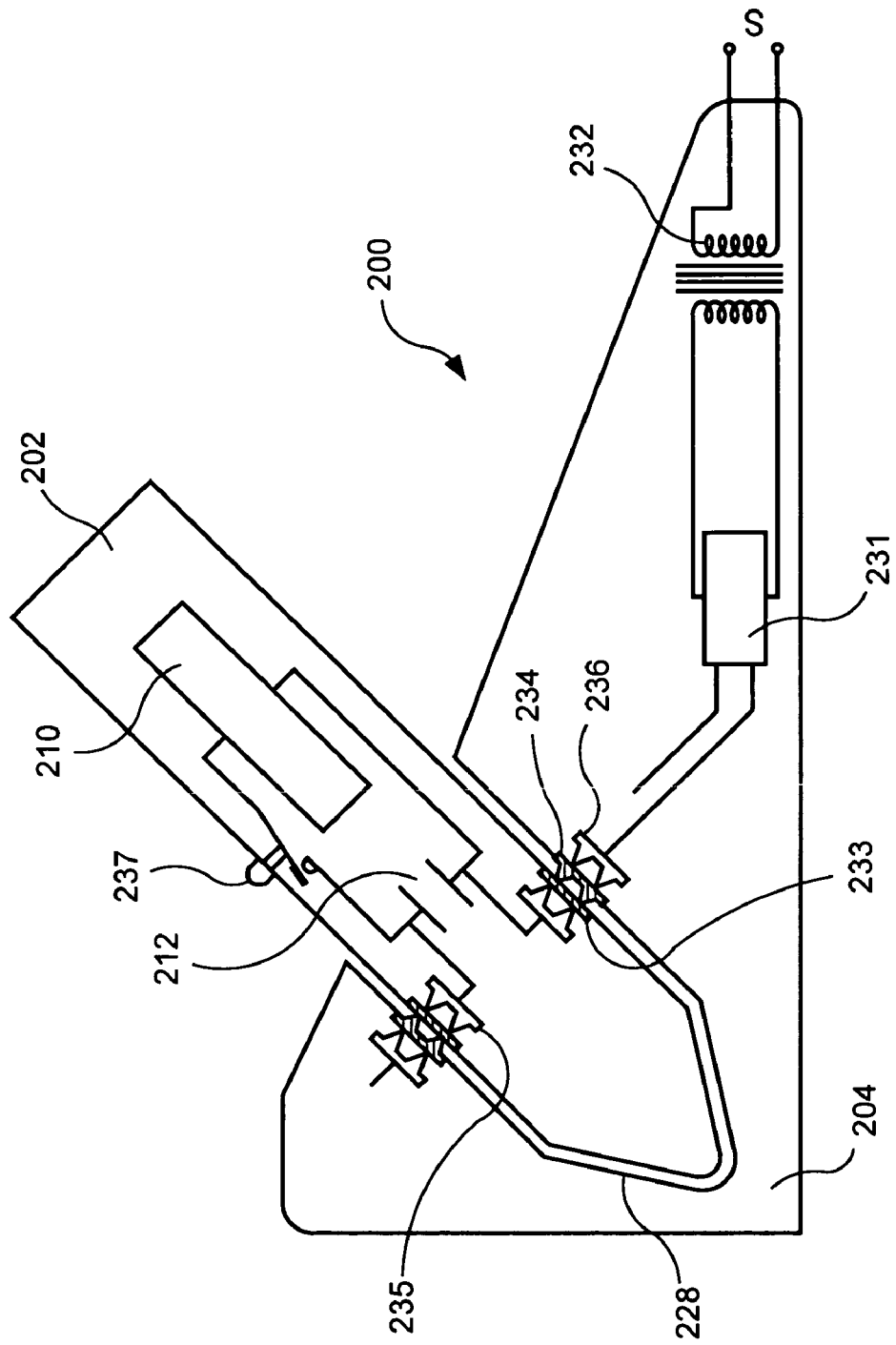
FIG. 17 illustrates an operational position of the laser perforator assembly.

FIGS. 14, 15, and 17 illustrate alternative ways of focusing a laser beam at the optimal depth by means of controlled positioning of the skin site at the predetermined distance from the focusing arrangement. In the arrangement of FIG. 14, after a low intensity visible spectrum light beam is discharged from the source 180 and tangentially engages a skin site to be perforated, it is registered by the receiver 182. This triggers an electric signal directed to the power supply block 184, so that the laser source 186 is activated discharging the laser beam, which is directed at the area of engagement between the light beam and the skin. Thus, skin perforation occurs instantaneously.

In the embodiment of FIG. 15, a low intensity visible spectrum light beam is discharged from the source 180 at an angle to the skin surface. Upon reflection from the skin it is registered by the receiver 182, generating the electrical signal directed to the power supply unit. Thus, the laser source 186 is energized, so that the laser beam is discharged targeted to the skin area initially receiving the light beam of visible spectrum.

Figure 16:
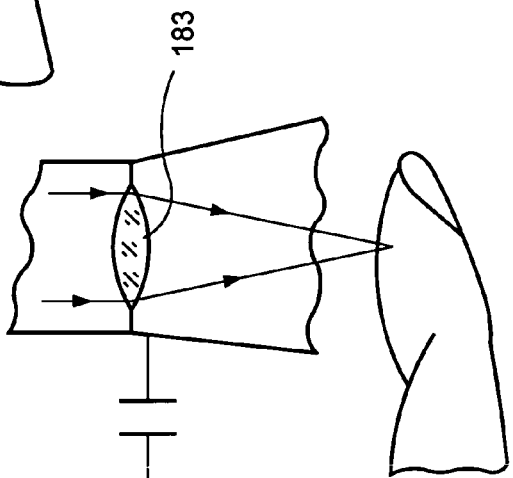
FIG. 16 illustrates a further focusing arrangement of the invention.

According to FIG. 16, the required distance between the skin site and the perforation device is controlled by means of a capacity sensor. Thus, when the focusing system is set at the required distance from the skin surface, the capacity sensor will be disturbed, and an electric signal is generated to energize the laser.

Figure 18:
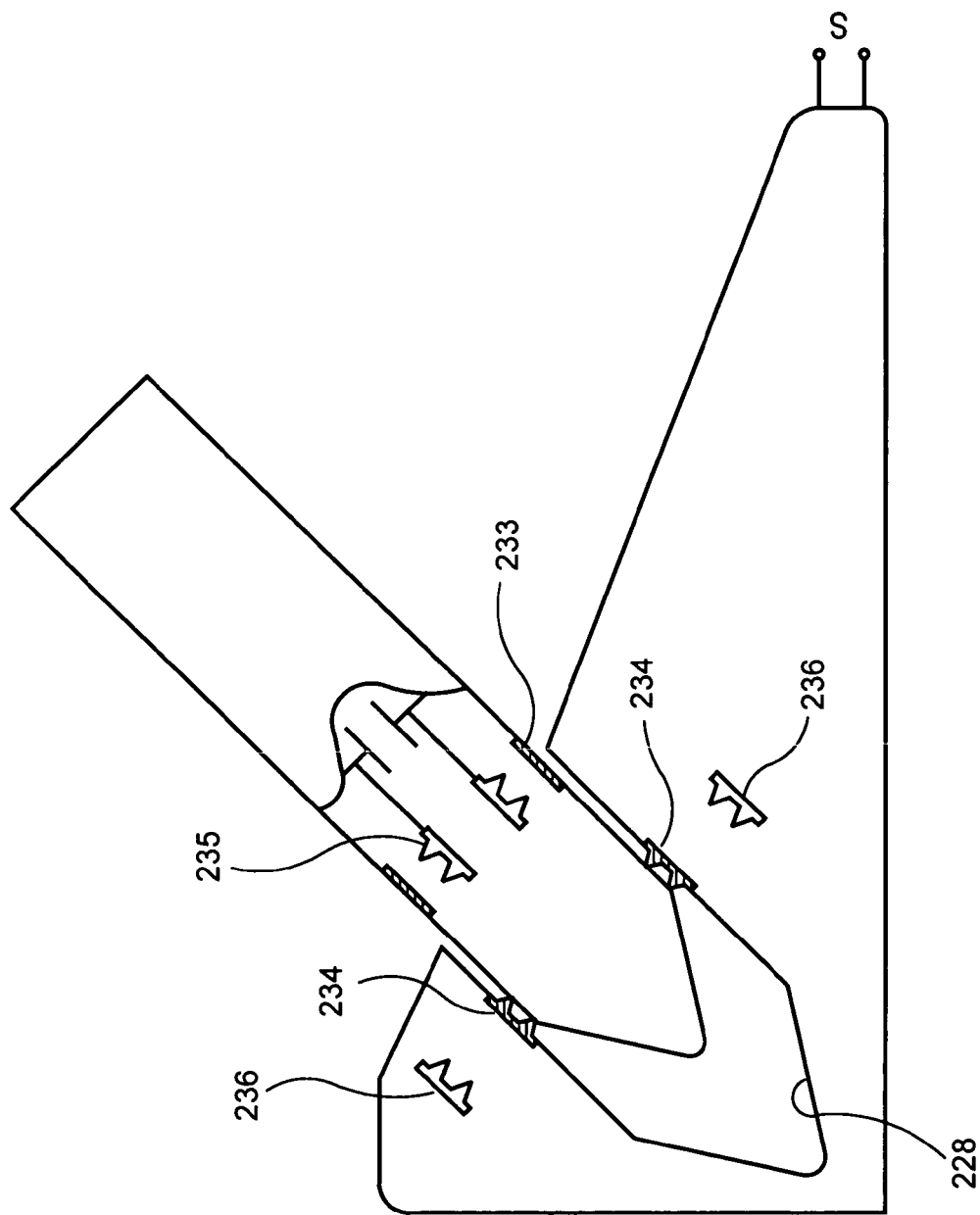
FIG. 18 illustrates the assembly of FIG. 17 with the housing prior to its full insertion into the receiving cavity of the base.

Turning now to FIGS. 17 and 18 which illustrate a compact laser perforator 200 with a lightweight hand-held housing 202 which is separable from the energy supply base 204. The base is provided both for charging of a rechargeable power unit 210 positioned within the housing as well as for storage of the housing when the laser perforator is not in use. The cavity 228 extends downwardly from an upper portion of the base and is shaped and sized to receive at least a portion of the hand-held housing 202.

As clearly illustrated in FIGS. 17 and 18 a laser source 210 and the rechargeable power unit which is in the form of the reservoir-capacitor 212 are positioned within the hand-held housing 202. An electrical converter 231 and a transformer 232 are placed within the power base. The reservoir-capacitor has a set of contacts 235 which correspond to the contacts 233 provided within the body of the hand-held housing. The receiving cavity 228 is formed with the matching contacts 234. In order to charge the reservoir-capacitor, the hand-held housing 202 containing the laser source is placed within the receiving cavity 208, so that the contacts 233 of the housing and the contacts 234 of the cavity are being connected. For safety reasons, as illustrated in FIG. 18, these contacts in their regular position have a zero potential and are not connected to the electrical circuitry of the perforator. When the housing is placed into the receiving cavity 208 (see FIG. 17), the contacts 233 and 234 are connected to the contacts 235 and 236. Thus, the reservoir-capacitor and the laser source become connected to the electrical power supply circuit. In the above-discussed arrangement, there is no open access to the contacts 235 and 236. Therefore, as illustrated in FIG. 18, when the housing 202 is withdrawn from the receiving cavity 208, the contacts 235 are moved inwardly, so that there is no connection between these contacts and the exterior of the housing. In a similar manner, in this position the contacts 236 are moved inwardly within the power base, so that there is no direct connection between these contacts and the receiving cavity. Upon complete insertion of the housing 202 within the receiving cavity 208, the reservoir-capacitor 212 is charged to the required level. Then, the housing can be removed from the power base and the laser source is activated by pressing the button 237.

Figure 19:
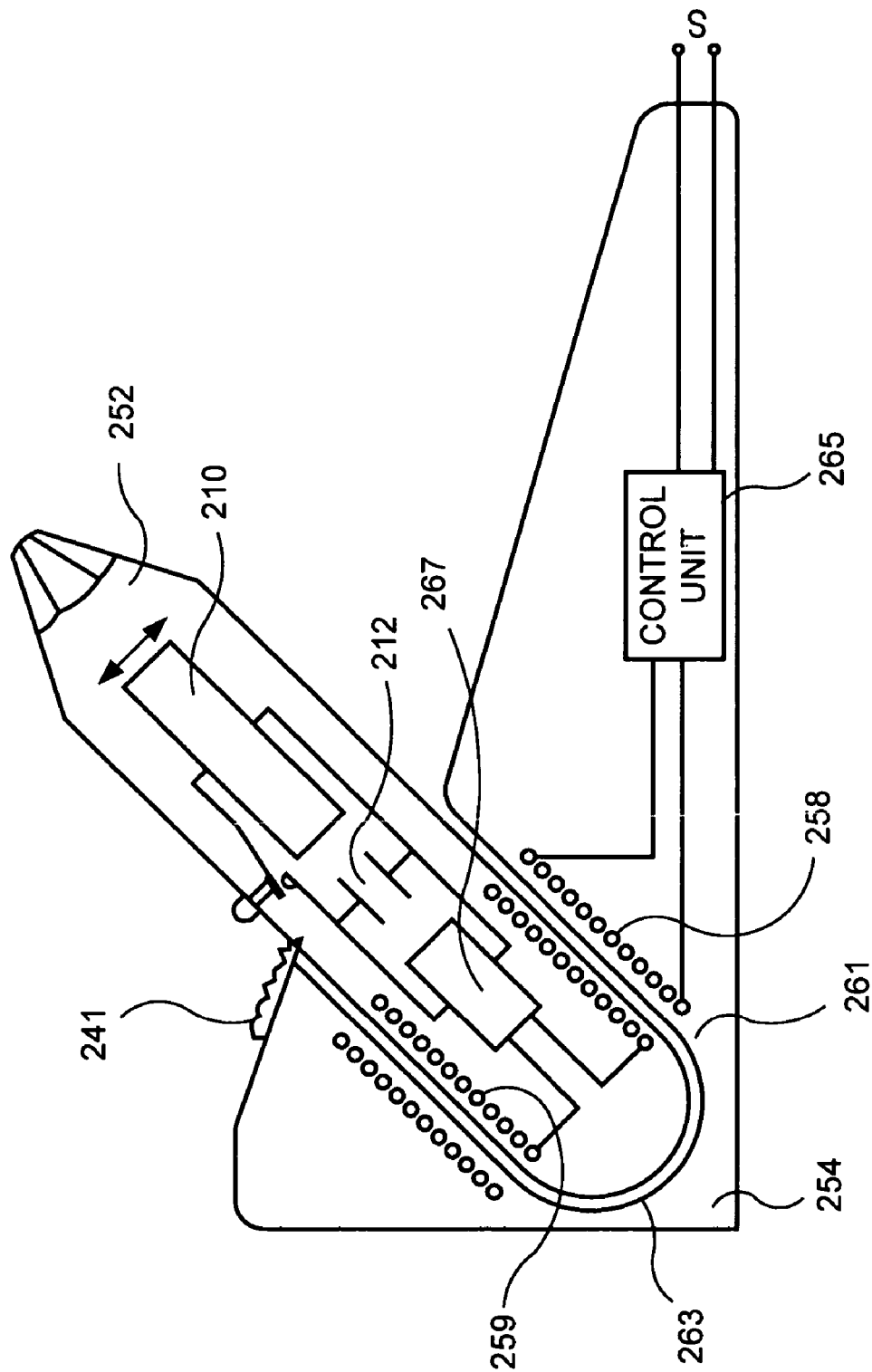
FIG. 19 shows another embodiment of the laser perforator assembly of the invention.
Figure 21:
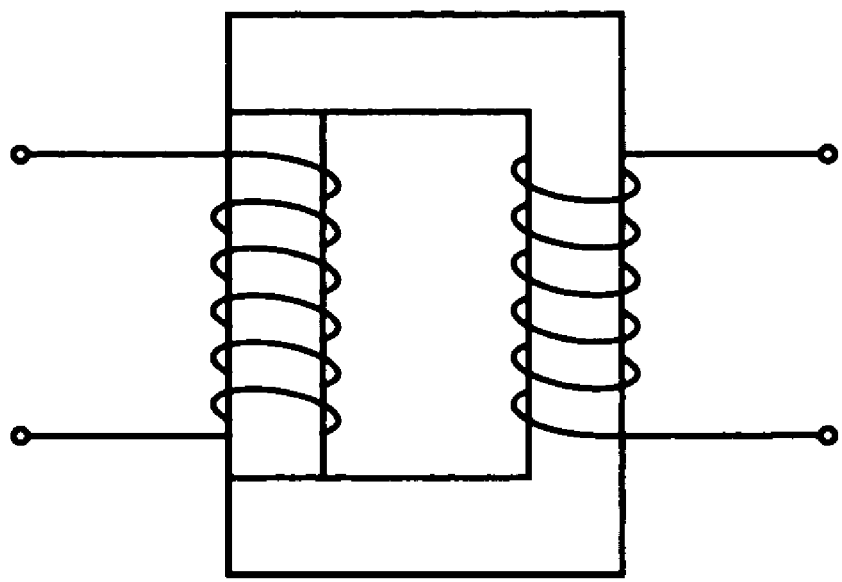
FIG. 21 shows another winding arrangement of the transformer of FIG. 20.
Figure 20:
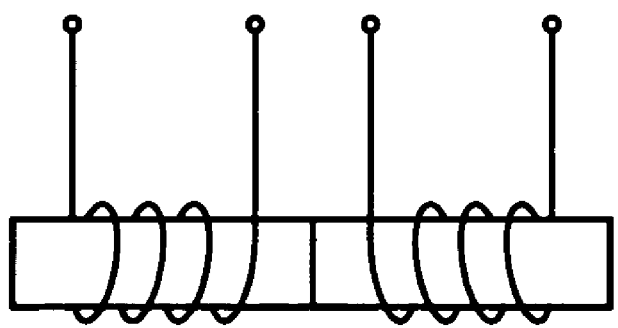
FIG. 20 shows one winding arrangement used of a transformer of FIG. 19.

Turning now to FIGS. 19-21 which illustrate another embodiment of the laser skin perforator assembly of the invention. Similar to the embodiment of FIGS. 17 and 18, the assembly consists of two main independent parts: a hand-held housing 252 and a power base 254. In this embodiment a transformer 261 is divided into two individual units. The first unit containing the primary winding 258 and the control unit 231 is situated within the inner area of the power base 254. The second unit of the transformer including the secondary winding 259 is situated within the hand-held housing 252. Among other major elements situated in the hand-held housing are: a rechargeable power unit in the form of a reservoir capacitor 212, an electrical converter 267 and a laser source 210.

A receiving cavity projects downwardly from the upper portion of the base. The cavity is shaped and sized to receive at least a low end portion of the hand-held housing. An inner area of the base surrounding the receiving cavity defines a compartment which is adapted to accommodate a primary coil assembly 258. The primary coil can be wound around an electrically-insulative but magnetically-conductive bobbin.

This design eliminates the need for open electrical contacts, similar to the contacts 33, 34 of FIGS. 17 and 18 further enhancing the electrical safety of the perforator. To further improve transformation ratio of the transformer 261, a locking mechanism 241 can be provided for fixedly positioning of the hand-held housing in the predetermined position within the receiving cavity of the power base. For charging of the reservoir-capacitor, the hand-held housing is placed into the receiving cavity of the of the power base unit (see FIG. 8), so as to connect the primary winding to the AC power supply and to provide the required voltage inside the secondary winding disposed in the housing. When the voltage within the winding reaches the level predetermined by the control unit (which corresponds to full charge of the reservoir capacitor) the charging process is terminated. The perforator is now ready for use and can be removed from the receiving cavity. The secondary winding can be arranged in line with the primary winding, as illustrated in FIG. 21, or in parallel with the primary winding as shown in FIG. 22. Furthermore, the secondary winding can be in the form of a coreless arrangement or can have a core. This design with separated windings of the transformer excludes the necessity of direct open electric contacts between the housing and the power base. This arrangement assures safe operation and charging of the "wireless" laser emitter.

What is claimed is:

1. A laser skin perforator comprising: a laser light source for generating an output laser beam, a focusing arrangement for focusing the output laser beam at a skin area selected for perforation, a retaining arrangement for retaining said skin area, said retaining arrangement being formed to intensify blood circulation within said skin area selected for perforation and a device for preventing an accidental activation of the laser source when said laser skin perforator does not engage said skin area;

said device including a forwardly positioned engaging cup comprising a plurality of independent engaging segments slidably arranged along a longitudinal axis thereof, a distal portion of each said segment forming a part of a switch operable between open and closed positions thereof, wherein in the open position of the switch the distal portions of engaging segments are spaced from a conductive plate positioned rearwardly of the engaging cup, so as to disconnect electric supply from said laser source, and in said closed position the distal portions of the engaging segments engage the conductive plate so as to activate the electric supply.

2. The laser perforator of claim 1, wherein said device further comprises a sliding member movable within a plane transverse to the direction of the laser beam, wherein, in a standard position of the device said sliding member blocks a central passage of the perforator thus preventing an accidental discharge of the laser beam.

3. The laser perforator of claim 2, wherein said device is selected from the group consisting of a photo sensor and an electric capacity sensor.

4. The laser perforator of claim 1, further comprising:
a rechargeable power supply unit, said laser source and said rechargeable power supply unit are situated within a first hand-held housing, and a power supply unit is situated within a second housing independent from the first housing, wherein there is no permanent electrical connection between the first and second housings.

5. The laser skin perforator of claim 4, wherein said laser source and said power supply unit are temporarily electrically connected for charging of the rechargeable power supply unit by internal and external contacts, said external contacts are being disconnected from electrical circuits.

6. The laser skin perforator of claim 5, wherein the temporary connection between the laser source and the power supply circuit is carried out by electrically neutral contacts and by mechanical, electromagnetic, magnetic and/or optical commutation devices.

7. The laser perforator of claim 4, wherein said power supply unit contains a transformer, so that a primary winding of the transformer is positioned within the housing containing the power supply unit and the secondary winding of the transformer is positioned within the housing containing the laser source.

8. The laser perforator of claim 7, wherein in said transformer the secondary winding is in line or in parallel with the primary winding.

9. The laser perforator of claim 7, further comprising a connecting mechanism for fixedly connecting the first hand-held housing containing the laser source within the second housing containing said power supply.

10. The laser perforator of claim 4, further comprising a device for preventing accidental activation of the laser source when the laser skin perforator does not engage the skin area selected for perforation.

11. The laser perforator of claim 1, wherein said engaging cup is formed within an inner cavity adapted to receive said plurality of engaging segments.

12. The laser perforator of claim 11, wherein each said segment is adapted for slidable movement within the inner cavity along the longitudinal axis of the engaging cup independently of the remaining segments.

* * * * *